(12) United States Patent
Gießibl (10) Patent No.: US 9,347,845 B2
(45) Date of Patent: May 24, 2016

(54) MAGNETO-ELASTIC SENSOR, LOAD PIN, BALL-JOINT AND TOW COUPLING COMPRISING THIS SENSOR, METHOD OF DETERMINING A DIRECTION OF A LOAD VECTOR

(71) Applicant: Methode Electronics Malta Ltd, Mriehel (MT)

(72) Inventor: Johannes Gießibl, Mriehel (MT)

(73) Assignee: Methode Electronics Malta Ltd., Mriehel (MT)

( * ) Notice: Subject to any disclaimer, the term of this patent is extended or adjusted under 35 U.S.C. 154(b) by 0 days.

(21) Appl. No.: 14/251,760

(22) Filed: Apr. 14, 2014

(65) Prior Publication Data

US 2014/0360282 A1    Dec. 11, 2014

(30) Foreign Application Priority Data

Apr. 15, 2013   (EP) .................................... 13163832

(51) Int. Cl.

| | |
|---|---|
| *G01B 7/16* | (2006.01) |
| *G01L 9/00* | (2006.01) |
| *B60D 1/24* | (2006.01) |
| *F16C 11/06* | (2006.01) |
| *G01N 27/72* | (2006.01) |
| *G01P 13/02* | (2006.01) |
| *G01L 1/12* | (2006.01) |
| *G01L 3/10* | (2006.01) |

(52) U.S. Cl.
CPC .............. *G01L 9/0001* (2013.01); *B60D 1/248* (2013.01); *F16C 11/06* (2013.01); *G01L 1/125* (2013.01); *G01N 27/72* (2013.01); *G01P 13/02* (2013.01); *G01L 3/102* (2013.01); *Y10T 403/20* (2015.01)

(58) Field of Classification Search
CPC ....... G01L 9/0001; G01L 1/125; G01L 3/102; G01N 27/72
USPC ................. 73/779, 862.331–862.335, 862.69
See application file for complete search history.

(56) References Cited

U.S. PATENT DOCUMENTS

| | | | |
|---|---|---|---|
| 6,330,833 B1 * | 12/2001 | Opie et al. ............... | 73/862.333 |
| 6,341,534 B1 * | 1/2002 | Dombrowski ........... | 73/862.333 |
| 2009/0212770 A1 * | 8/2009 | Koyama ....................... | 324/249 |

(Continued)

FOREIGN PATENT DOCUMENTS

EP            0525551        2/1993

OTHER PUBLICATIONS

Extended European Search Report dated Sep. 19, 2013, in European Patent Application No. 13163832.2.

*Primary Examiner* — Max Noori
(74) *Attorney, Agent, or Firm* — Plumsea Law Group, LLC (57) ABSTRACT

A magneto elastic sensor having a longitudinally extending shaft like member which is subject to a load, is provided. A magneto-elastically active region is directly or indirectly attached to or forming a part of the member in such a manner that the mechanic stress is transmitted to the active region. A magnetically polarized region of the active region becomes increasingly helically shaped as the application stress increases. A magnetic field sensor is arranged approximate the magneto-elastically active region for outputting a signal corresponding to a stress induced magnetic flux emanating from the magnetically polarized region. The magnetic sensor determines one out of a shear stress and a compressive stress. The magnetic sensor can include at least one direction sensitive magnetic field sensor, which is arranged having a predetermined and fixed spatial coordination with the member.

13 Claims, 8 Drawing Sheets

(56) References Cited

U.S. PATENT DOCUMENTS

2009/0230953 A1 9/2009 Lee
2010/0242626 A1* 9/2010 Weng .................. 73/862.333
2012/0074933 A1* 3/2012 Lee .............................. 324/244
2013/0091959 A1* 4/2013 Lee ..................... G01L 3/1435
73/862.335
2013/0125669 A1* 5/2013 Barraco et al. ........... 73/862.333

* cited by examiner

MAGNETO-ELASTIC SENSOR, LOAD PIN, BALL-JOINT AND TOW COUPLING COMPRISING THIS SENSOR, METHOD OF DETERMINING A DIRECTION OF A LOAD VECTOR

FIELD OF THE INVENTION

The invention is related in general to systems and methods involving the use of magnetic field sensors for measuring a load. In particular, the invention is related to a magneto-elastic sensor, a load pin, a ball joint and a tow coupling incorporating this sensor. Furthermore, the invention relates to a method of determining a direction of a load vector.

DESCRIPTION OF THE RELATED ART

In the control of systems having a member, which is subject to mechanic forces, the determination of the mechanic load is one of the fundamental parameters of interest. The sensing of the load, the torque, bending, and/or shear stress should be performed in an accurate, reliable and inexpensive manner.

Previously, the measurement of mechanic load was accomplished using contact-type sensors, which are directly attached to the member or are incorporated in said member. A typical contact-type sensor is a strain-gauge. This detector is directly attached to a surface of the member or is incorporated in the member. For example, a strain-gauge is attached to a surface of a shaft. The electrical resistance of this device changes, when the strain-gauge undergoes a certain strain.

A typical application of a strain-gauge is a load pin, which is a transducer used to measure load and force and to provide overload protection. The load pins may be mounted into machines in place of normal shafts. They are typically fitted with strain-gauges, allowing them to produce a signal proportional to the measured load.

However, strain-gauges are relatively unstable and offer a limited reliability due to the necessary direct mechanical contact with the member taking up the load. In addition to this, the measurement values of strain-gauges tend to drift, thereby limiting the reliability, in particular for long term measurements.

As an alternative to the widely used strain-gauges, non-contact type sensors exploiting the magneto-elastic effect were developed. These are frequently applied for torque measurements at rotating shafts in various mechanic systems. For example, U.S. Pat. No. 6,553,847 B2 of Garshelis, the disclosure of which is incorporated herein by reference in its entirety, discloses a magneto-elastic torque sensor, which provides an output signal indicative of the applied torque. Another sensor for measuring the torque, which is applied to a rotating shaft, is disclosed in U.S. Pat. No. 5,351,555 of Garshelis, the disclosure of which is incorporated herein by reference in its entirety. In the U.S. '555 patent, the magneto-elastically active region resides in an annular member surrounding the shaft. This annular member comprises magnetic material endowed with an effective uniaxial magnetic anisotropy in circumferential direction. When the shaft is subject to a torque, the stress induced in the shaft is transferred to the annular member, which is rigidly connected to the shaft. In the U.S. '847 patent, the material of the shaft itself is magnetically polarized in circumferential direction. Therefore, this sensor dispenses with the separate ring comprising the magnetic material. Within both systems, the magnetic field sensors are mounted proximate to the magnetoelasticly active region, in order to sense the magnetic field emanating from this region. Upon application of a torsional stress to the shaft, the circumferentially directed magnetization reorients and becomes increasingly helical as the torsional stress increases.

U.S. Pat. No. 2012/0074933 A1, the disclosure of which is incorporated herein by reference in its entirety, discloses a non-contact sensor of the magnetoelasticly type comprising a plurality of sensors, which are arranged around the circumference of a shaft. The magnetic field sensors are stationary while the shaft is rotating. As a result, each sensor is repeatedly exposed to the magnetic field emanating from a certain area of the magnetically polarized region. This provides an averaging effect to the measurement value of the strain. This is because for determination of the value of the strain, the signals of the individual sensors are averaged. Thus, residual inhomogeneities of the magnetic polarization are averaged out.

In summary, all prior art concepts either apply conventional strain-gauges or have one or more static magnetic field sensors cooperating with a rotating shaft comprising the magnetically polarized region.

Based on the foregoing, there is a need for a new and better technique for effectively measuring stress and strain in systems having a member, which is typically non-rotating, but which is subject to a mechanic load.

SUMMARY

In one aspect of the invention, a magneto-elastic sensor comprising a longitudinally extending shaft like member having at least one magneto-elastically active region and a magnetic field sensor means is provided. The longitudinally extending shaft like member is subject to a load introducing mechanic stress in said member. The at least one magneto-elastically active region is directly or indirectly attached to the shaft like member. However, the at least one magneto-elastically active region may also form a part of said member. The magneto-elastically active region is arranged in such a manner that the mechanic stress is transmitted to the active region. Said region comprises at least one magnetically polarized region such that the magnetic polarization becomes increasingly helically shaped as the applied stress increases. The magnetic field sensor means is arranged approximate the at least one magneto-elastically active region. The magnetic field sensor means is further configured for outputting a signal corresponding to a stress-induced magnetic flux, which emanates from the magnetically polarized region. The sensor according to aspects of the invention comprises a magnetic sensor means comprising at least one direction sensitive magnetic field sensor. This direction sensitive magnetic field sensor is configured for determination of a shear stress and/or of a tensile or compressive stress. In particular, the direction sensitive magnetic field sensor is arranged to have a predetermined and fixed spatial coordination with the member.

Advantageously, the magneto-elastic sensor according to aspects of the invention dispenses with a mechanical linkage or connection between the sensor means and the shaft member. This eliminates sources of error, which result from mechanic failure of this connection. The sensor reliably operates even under extreme operating conditions. The drift of the measurement values during long term measurement is reduced. The sensor according to aspects of the invention is versatile in that it may be applied to or integrated in nearly every shaft like member, which may be for example a part of a hydraulic unit of a land-, marine-, rail- or air transport vehicle.

According to an advantageous embodiment of the invention, the sensing direction of the at least one direction sensitive magnetic field sensor is arranged in that the sensing direction is at least substantially parallel to a tangential direction of the shaft like member. The magneto-elastically active region, when exposed to a normal force, emanates a stress induced magnetic flux having a component directed in tangential direction of the shaft. In conventional sensor systems, which exploit the magneto-elastic effect, the tangential component of the magnetic field vector is neglected. This is mainly due to the fact that these traditional sensors are torque sensors measuring shear stress. In this situation, the torque induced magnetic field vector is substantially parallel to an axial direction of the shaft. However, the magneto-elastic sensor according to aspects of the invention senses the tangential component of the magnetic field vector and is therefore capable of determining normal stress, which may be a tensile or compressive stress in the shaft like member. This type of stress may be due to bending of the shaft or exposure to an axial load. In other words, the tensile and compressive stress is preferably due to forces, which are applied substantially in axial direction of the shaft.

According to another embodiment of the invention, the at least one magnetic field sensor of the magnetic sensor means is arranged in that the sensing direction of said sensor is at least substantially parallel to a radial direction of the shaft like member. The radial component of the stress induced magnetic field evolves from all stress types, which are induced in the shaft like member. In other words, shear stress and normal stress both induce a magnetic field vector emanating from the active region, said field vector having a radial component. Consequently, the magneto-elastic sensor according to this particular embodiment of the invention is sensitive to all stress types. The embodiment is particularly suitable, if the shaft is exposed to only one single type of stress.

According to still another embodiment of the invention, the magnetic sensor means comprises a first direction sensitive magnetic field sensor and a second direction sensitive magnetic field sensor. The first and the second sensor are arranged in that they have 180° opposite sensing directions. This "vice versa" configuration of the magnetic field sensors enables the magneto-elastic sensor according to this embodiment to distinguish between the different directions of the applied stress and mechanic load. For example, compressive and tensile stresses are distinguishable, if the measurement data, which is acquired from the first and the second sensor, is differentially processed.

In another embodiment of the invention, the first and the second magnetic field sensor are arranged approximate to opposite sides of the magneto-elastically active region, respectively. These sides of the active region are opposite to each other with respect to the shaft axis. A side of the active region may be an interior surface or wall of the shaft as well as an exterior wall or surface of the shaft like member. This depends on the particular configuration of the sensor means. When, for example, the sensors of the sensor means are arranged in the interior of a hollow shaft like member, the sides will be opposite surfaces of the cavity inside the member. When the sensors are arranged exterior to the shaft like member, opposite sides are the outer surfaces of the shaft, which are opposite with respect to the shaft axis. In this particular sensor arrangement, the sensor means is suitable for acquiring stresses and loads in axial direction of the shaft, i.e. tensile and compressive stress. Preferably, the first and the second sensing direction may be arranged in that they are substantially perpendicular to the shaft axis.

According to another advantageous aspect of the invention, the magneto-elastic sensor comprises a sensor means having at least four magnetic field sensors. These four sensors have a first to fourth sensing direction. The first to fourth sensor are arranged in that the first to fourth sensing direction and the shaft axis are at least substantially parallel to each other. Furthermore, the first to fourth magnetic field sensor is arranged along the circumference of the shaft having substantially equal distances in circumferential direction between each other. In particular, the first and third magnetic field sensor is arranged opposite to each other with respect to the shaft axis. The first and third sensing direction may be arranged to be 180° opposite to each other. Furthermore, the second and fourth magnetic field sensor may be arranged opposite to each other with respect to the shaft axis. The second and fourth sensing direction may be arranged 180° opposite to each other.

According to this embodiment of the invention, the sensor means is configured for determination of a first component and a second component of the load, which is applied to the shaft like member. In particular, the first and third magnetic field sensor can form a first group of sensors and the second and fourth magnetic field sensor can form a second group of sensors. If considered in a Cartesian coordinate system, the first group of sensors is suitable for determination of a load component, which is directed along a first Cartesian axis, for example the X-axis. The second group of sensors senses a component of the load, which is substantially perpendicular to the first component. If this is considered in the same Cartesian coordinate system, the second group of sensors senses the force component in Y-direction. In other words, the X- and Y-component of the load may be determined. Consequently, the direction and the value of the stress or force, which is applied to the shaft like member, may be determined from said components for example in a Cartesian coordinate system.

According to still another aspect of the invention, the shaft like member comprises a first magneto-elastically active region and a second magneto-elastically active region. Similar to the other embodiments of the invention, these are directly or indirectly attached to or form a part of the member in such a manner that the mechanic stress is transmitted to the active regions. A respective one of the active regions comprises a magnetically polarized region. The magnetic polarization of the first active region is substantially opposite to the magnetic polarization of the second active region. The magnetic sensor means comprises a first pair of magnetic sensors and a second pair of magnetic sensors. Each pair comprises a first and a second direction sensitive magnetic field sensor. The sensors of the first and second pair being arranged approximate the first and second magneto-elastically active region, respectively. The first sensor pair outputs a first signal corresponding to a stress-induced magnetic flux emanating from the first magnetically polarized region. Similarly, the second pair of magnetic field sensors outputs a second signal corresponding to a stress-induced magnetic flux emanating from the second magnetically polarized region. A control unit of the magneto-elastic sensor is configured for determination of the stress applied to the member. The control unit performs a differential evaluation of the signals of the first pair of sensors and the second pair of sensors.

The differential evaluation of the signals advantageously doubles the signal, which is correlated with the applied stress. Because the polarization of the first and second magnetically active region is opposite to each other, theoretically possible external fields are compensated. The magneto-elastic sensor according to this embodiment is more sensitive and less susceptible to errors.

According to an embodiment of the invention, the member is an at least partially hollow shaft and all magnetic field sensors of the sensor means are entirely arranged inside the interior of the hollow shaft. This is advantageous, if there is limited construction space around the shaft like member. Furthermore, the magneto-elastic sensor is less susceptible to external fields because of a shielding effect of the shaft. In particular, the at least one magneto-elastically active region projects along the circumference of the member. Said region is magnetized in that the domain magnetizations in the magnetically polarized region lie within at most a plus or minus 45° limit of a circumferential direction of the member. Furthermore, the direction sensitive magnetic field sensors may be vector sensors. In particular, the vector sensors may be one of a Hall-effect, magneto-resistance, magneto-transistor, magneto-diode, MAGFET field sensors or fluxgate magnetometer. These aspects advantageously apply to all embodiments of the invention.

The sensor according to aspects of the invention is particularly suitable for incorporation in a load pin, a ball-joint or in a tow coupling, which may be part of a land based on road or off-road vehicle.

According to another aspect of the invention, a load pin having a longitudinally extending shaft like member incorporating a magneto-elastic sensor according to aspects of the invention is provided. Conventionally, load pins are equipped with strain-gauges having the well known technical deficiencies. The load pin according to aspects of the invention overcomes the drawback of the prior art solutions. In particular, the load pin does not tend to drift of the measurement values and is less error-prone.

Any hydraulic piston, crane application, car and other various applications incorporating bolts and pins, where shear forces are applied, may be equipped with the load pin according to aspects of the invention. Traditionally, shear force sensors using strain-gauges are designed in that they get intentionally weaken to provide enough deformation so as to allow a measurement of the applied loads. The magneto elastic shear-force sensor, however, provides the possibility to design the bolt without weaken locations and significantly higher overload capability. The load pin having the integrated magneto-elastic sensor provides the possibility to detect shear forces in pins, screws, bolts etc.

According to still another aspect of the invention, a ball-joint having a bearing stud and a socket, wherein the bearing stud comprises a longitudinally extending shaft like member incorporating a magneto-elastic sensor according to aspects of the invention, is provided. Ball-joints are typically subject to forces and stresses of various directions. The sensor according to aspects of the invention is advantageously suitable for determination of the direction of the force or stress, which is applied to the shaft like member of the ball-joint. In stabilizer links and steering systems, ball joints are used to connect moving components to provide flexibility. The detection of loads within the ball joints provides extended possibilities for future stability control systems, in particular in chassis applications. The ball joint having an integrated load sensor provides the possibility to detect load on stabilizer links, steerings, etc.

According to still another aspect of the invention, a tow coupling having a curved shaft and a tow ball is provided. The curved shaft comprises at least one longitudinally extending shaft like member incorporating a magneto-elastic sensor according to aspects of the invention. Similar to the ball-joint, the tow coupling is also subject to forces having various directions. The determination of said forces may be suitable so as to accomplish with safety requirements and for stability control. The detection of the applied load on tow couplings is desirable within the automotive industry. The magneto-elastic sensor according to aspects of the invention provides the possibility to achieve the recommended accuracies, cost targets and to fulfill environments specifications.

According to an advantageous embodiment, the curved shaft of the tow coupling comprises a first and a second longitudinal extending shaft like member. The shaft axis of the first and the second shaft like member are substantially perpendicular to each other. The first and the second shaft like member are each provided with a magneto-elastic sensor according to aspects of the invention. In particular, these sensors may be incorporated in the shaft like members. Advantageously, if two sensor systems are integrated in the tow coupling, a supporting force and a towing force may be detected. In addition to this, the corresponding transverse forces may be determined.

According to still another aspect of the invention, a method of determining a direction of a load vector is provided. Within said method, a magneto-elastic sensor according to aspects of the invention is provided. In other words, a sensor comprising a longitudinally extending shaft like member is provided, wherein said member is subject to the load introducing mechanic stress in the member. Furthermore, the shaft like member comprises at least one magneto-elastically active region, which is directly or indirectly attached to or forms a part of the member. This active region cooperates with the member such that the mechanic stress is transmitted to the active region. Said active region comprises at least one magnetically polarized region such that the polarization becomes increasingly helically shaped as the applied stress increases. A magnetic field sensor means is arranged approximate the at least one magneto-elastically active region. This is configured for outputting a signal corresponding to a stress induced magnetic flux emanating from the magnetically polarized region. The magnetic sensor means further comprises at least one direction sensitive magnetic field sensor. The magnetic field sensor is configured for determination of a shear stress and/or of a tensile or compressive stress. In particular, the magnetic field sensor is arranged to have a predetermined and fixed spatial coordination with the member.

Furthermore, within the method according to aspects of the invention, the longitudinally extending shaft like member is exposed to a load. Measurement data of the at least one direction sensitive magnetic field sensor is processed so as to determine a shear stress and/or of a tensile or compressive stress. In particular, a direction of the load vector may be determined from the measurement data on the one hand and the predetermined and known spatial coordination between the magnetic field sensor and the member on the other hand.

According to an advantageous embodiment of the invention, the sensor means comprises at least a first to fourth magnetic field sensor having a first to fourth sensing direction. The sensing directions and the shaft axis are at least substantially parallel to each other. The first to fourth magnetic field sensor is arranged along the circumference of the shaft having substantially equal distances in circumferential direction between each other. The method according to this embodiment of the invention further incorporates processing of measurement data of the first and third magnetic field sensor so as to determine a first component of the load vector. Furthermore, the method incorporates processing of measurement data of the second and fourth magnetic field sensor so as to determine a second component of the load vector. A direction of the load vector is determined from the first and second component and the predetermined and known spatial coordination of the first to fourth magnetic field sensor with respect to the member.

In another embodiment of the invention, a magneto-elastic sensor is provided having a member, which comprises a first magneto-elastically active region and a second magneto-elastically active region. These are directly or indirectly attached to or form a part of the member in such a manner that the mechanic stress is transmitted to the active regions. Each active region comprises a magnetically polarized region, wherein the magnetic polarization of the first active region and the magnetic polarization of the second active region are substantially opposite to each other. The magnetic sensor means comprises a first pair of magnetic sensors comprising a first and a second magnetic field sensor being arranged approximate the first magneto-elastically active region. This first pair outputs a first signal corresponding to a stress-induced magnetic flux emanating from the first magnetically polarized region. The magnetic sensor means further comprises a second pair of magnetic sensors comprising a first and a second magnetic field sensor. These are arranged approximate the second magneto-elastically active region for outputting a second signal. This second signal corresponds to a stress-induced magnetic flux emanating from the second magnetically polarized region. A differential evaluation of the two signals, i.e. of the first pair of the sensors and the second pair of sensors, is performed. The stress, which is applied to the member, is determined from this differential measurement and the corresponding evaluation.

Same or similar advantages which have been already mentioned with respect to the magneto-elastic sensor according to aspects of the invention apply in a same or similar way to the method of determining a direction of the load vector and will be not repeated.

BRIEF DESCRIPTION OF DRAWINGS

Further aspects and characteristics of the invention ensue from the following description of the preferred embodiments of the invention with reference to the accompanying drawings, wherein.

DETAILED DESCRIPTION OF EXAMPLE EMBODIMENTS

Figure 1A:
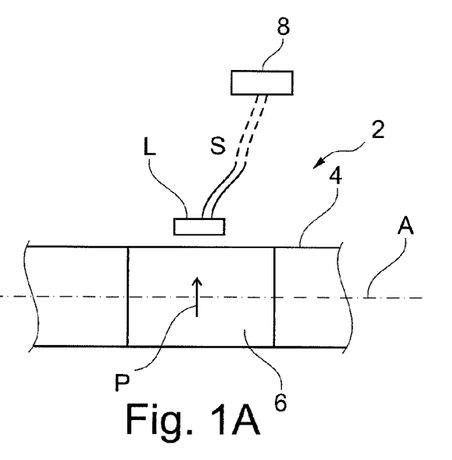
FIG. 1A shows a simplified side view of a magneto-elastic sensor configuration according to embodiments of the invention.
Figure 1B:
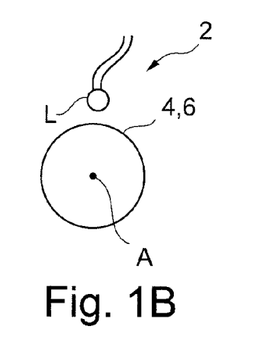
FIG. 1B shows a simplified cross sectional view of a magneto-elastic sensor configuration according to embodiments of the invention.

FIG. 1 A) is a simplified side view of a magneto elastic sensor 2 according to an embodiment of the invention. A rotating shaft like member 4 is provided with a magneto-elastically active region 6 having a circumferential polarization P, the direction of which is indicated by an arrow. When the shaft 4 is subject to a shear stress, which means for example that the shaft portion left from the active region 6 is urged to in a first direction and the shaft portion right from the active region 6 is subject to a counteracting force urging the shaft in opposite direction, the magnetic flux vector emanating from the active region 4 has a component, which is directed in axial direction of the shaft 4. The sensor L detects this component of the shear stress induced magnetic field and outputs a signal S. A processing unit 8 is configured to process this signal S so as to determine the stress, which is applied to the shaft 4. The sensor L has a sensing direction, which is substantially parallel to a shaft axis A shown in a dash-dotted line. The simplified cross section of FIG. 1 B) further illustrates the arrangement of the sensor L with respect to the shaft 4.

Figure 2A:
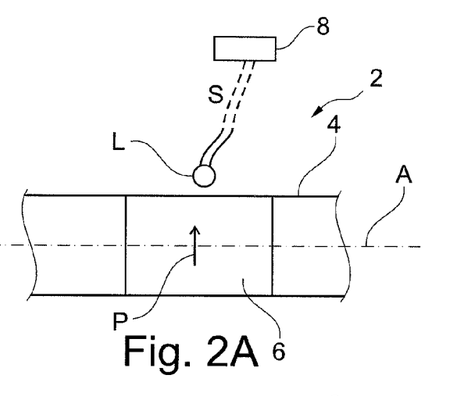
FIG. 2A shows a simplified side view of a magneto-elastic sensor configuration according to embodiments of the invention.
Figure 2B:
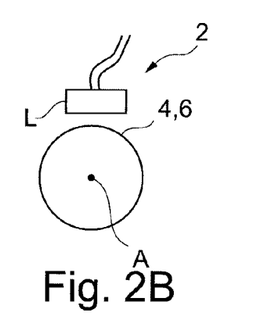
FIG. 2B shows a simplified cross sectional view of a magneto-elastic sensor configuration according to embodiments of the invention.

When the shaft 4 is subject to a force, which does not introduce a shear stress, for example: a bending force or a load in axial direction, the configuration shown in FIG. 2 A) and FIG. 2 B) is capable of determining this load. In FIG. 2 A), there is a simplified side view showing a sensor 2, according to this embodiment of the invention. The magneto elastic sensor 2 comprises a longitudinally extending shaft like member 4, which is subject to a load introducing a tensile or a compressive stress in the magneto-elastically active region 6. The shaft 4 may be a rotating or a non rotating part. For example, it may be a part of a pin or bolt. However, the shaft like member 4 may also be a rotating part, for example a transmission shaft. The polarization P of the active region 6 becomes increasingly helically shaped as the applied stress increases. In particular, a magnetic field emanating from the magnetically polarized region of the active region 6 exhibits a tangential component. This component of the stress induced magnetic field vector is detected using the direction sensitive sensor L. This sensor L may be arranged in a fixed spatial coordination with respect to the shaft like member 4. For example, the shaft 4 and the sensor L may have a timely constant spatial coordination with respect to each other.

The direction sensitive sensor L outputs a signal S, which is communicated to the processing unit 8. The measurement data of the direction sensitive sensor L is processed in that the direction and a value of the load is determined from the signal S and the predetermined and known spatial coordination between the member 4 and the sensor L. The tensile and compressive stress, which is applied in axial direction, is determined. The simplified cross section of FIG. 2 B) further illustrates the spatial coordination between the member 4 and the direction sensitive sensor L. The sensing direction is parallel to a tangent of the shaft 4. In other words, it is at least substantially perpendicular to the shaft axis A.

Figure 3A:
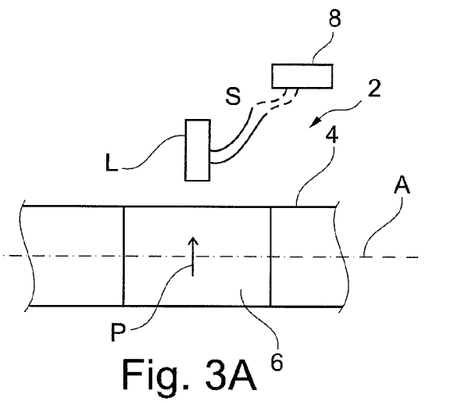
FIG. 3A shows a simplified side view of a magneto-elastic sensor configuration according to embodiments of the invention.
Figure 3B:
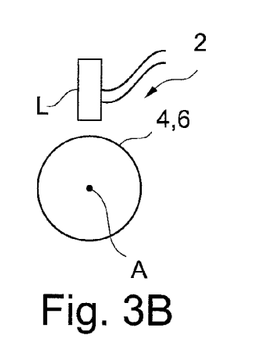
FIG. 3B shows a simplified cross sectional view of a magneto-elastic sensor configuration according to embodiments of the invention.

In FIG. 3 A), there is another simplified side view of a magneto-elastic sensor 2, according to another embodiment of the invention. The shaft like member 4 is configured similar to the embodiment of FIG. 2. However, the direction sensitive sensor L is arranged to have a sensing direction, which is parallel to the radius of the shaft 4. The simplified cross section of FIG. 3 B) further illustrates the spatial coordination between the member 4 and sensor L.

The magneto-elastic sensor 2 according to this embodiment of the invention is sensitive to all types of stress. The polarization P of the active region 6 becomes increasingly helically shaped as the applied stress increases. The stress induced magnetic field vector includes a radial component. Said radial component of the magnetic field vector is detected using the sensor L. The radial orientation is applicable in situations or applications when only one type of stress appears. This is a prerequisite for correct interpretation of the signal S in the processing unit 8. Otherwise, it might be impossible to distinguish between the different types of stress, for example between a torque and a tensile or compressive stress.

Figure 4A:
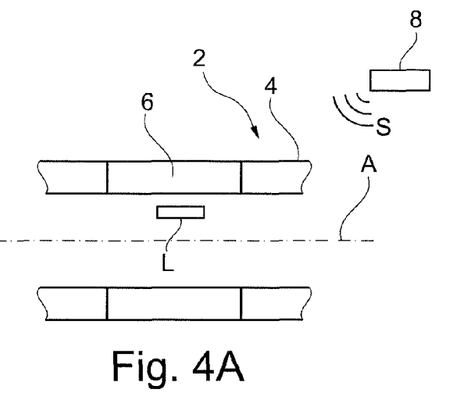
FIG. 4A shows a simplified axial cross section view of a magneto-elastic sensor configuration according to embodiments of the invention.
Figure 4B:
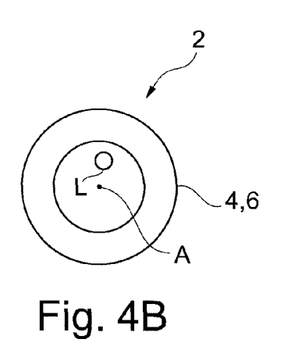
FIG. 4B shows a simplified cross sectional view of a magneto-elastic sensor configuration according to embodiments of the invention.

FIG. 4 A) shows another magneto elastic sensor 2, according to an embodiment of the invention. FIG. 4 B) is the corresponding cross section of this sensor 2. The shaft like member 4 is a hollow shaft, wherein the sensor L is arranged inside an interior space of the shaft 4. The sensing direction of the sensor L is parallel to the shaft axis A. The signal S of the sensor L is communicated to the processing unit 8 using any suitable data link, for example a wireless data link. Due to the axial orientation of the sensor L, a torque and/or a shear stress, which is applied to the shaft 4, is detectable. In particular, this embodiment is configured for detection of a shear stress or force.

Figure 5A:
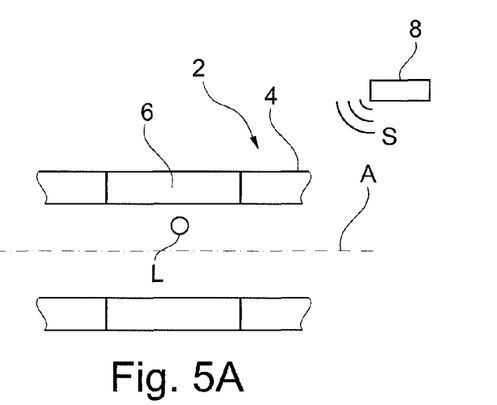
FIG. 5A shows a simplified axial cross section view of a magneto-elastic sensor configuration according to embodiments of the invention.
Figure 5B:
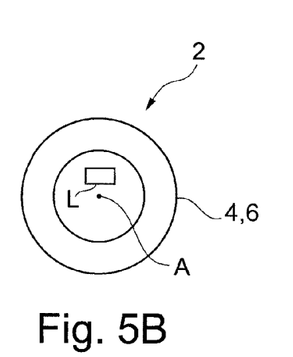
FIG. 5B shows a simplified cross sectional view of a magneto-elastic sensor configuration according to embodiments of the invention.

FIG. 5 A) is a simplified axial cross section of a magneto-elastic sensor 2 comprising a hollow shaft like member 4 incorporating a direction sensitive sensor L, according to an embodiment of the invention. The magnetic field sensor L is arranged in tangential direction with respect to the shaft 4. Similar to FIG. 2, the sensor 2 is suitable for measurement of tensile or compressive stress, which is applied to the hollow shaft 4. This type of stress may be due to bending of the shaft 4. Furthermore, the shaft 4 may be subject to a shear force. A force, which is applied along the shaft axis A, can also introduce a tensile or compressive stress. FIG. 5 B) is the simplified cross section, which corresponds to FIG. 5 A). The output signal S is communicated from the sensor L to the processing unit 8 for example via a wireless data link. The shaft 4 may be a non rotating part, such as a bolt for example, or it may be a rotating part, for example a torque transmitting shaft.

Figure 6A:
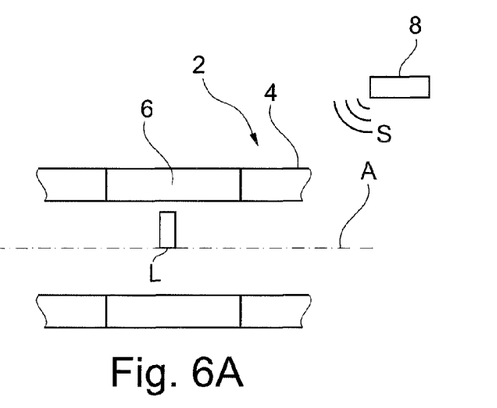
FIG. 6A shows a simplified axial cross section view of a magneto-elastic sensor configuration according to embodiments of the invention.
Figure 6B:
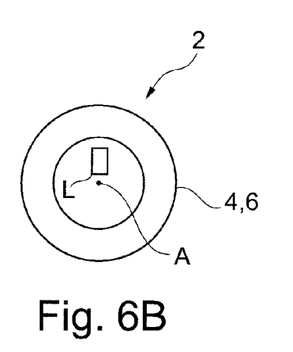
FIG. 6B shows a simplified cross sectional view of a magneto-elastic sensor configuration according to embodiments of the invention.

FIG. 6 A) is another simplified cross section of a magneto-elastic sensor 2, according to an embodiment of the invention. FIG. 6 B) shows the corresponding cross section of this sensor 2. Similar to the embodiment of FIG. 3, the sensor 2 of FIG. 6 is suitable for detection of any type of stress. This is due to the radial orientation of the magnetic field sensor L.

Figure 7:
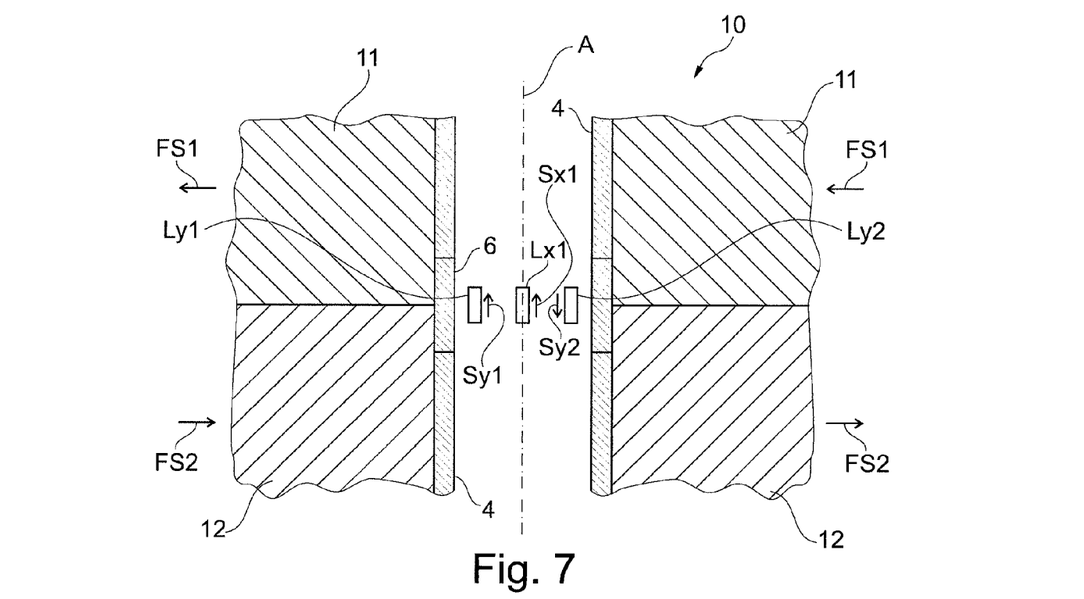
FIG. 7 is a simplified axial cross section of a load pin, according to an embodiment of the invention.

FIG. 7 is a simplified cross section of a load pin 10 according to an embodiment of the invention. The load pin 10 comprises a first or upper member 11, which is coupled to a second or lower member 12 via the shaft like member 4. The upper member 11 is subject to a first shear force FS1 pointing to the left. The lower member 12 is exposed to a second and opposite shear force FS2, pointing to the right. The shaft like member 4 comprises an active region 6, which is arranged at the transition between the upper and lower member 11, 12. Consequently, the active region 6 is subject to shear forces causing the magnetic flux emanating from the magnetically polarized region of said active region 6 to become increasingly helically shaped, when the shear forces FS1, FS2 increase. The sensor means of the load pin 10 comprises four direction sensitive magnetic field sensors LX1, LX2, LY1, LY2 being arranged along the inner circumference of the shaft like member 4.

Figure 8:
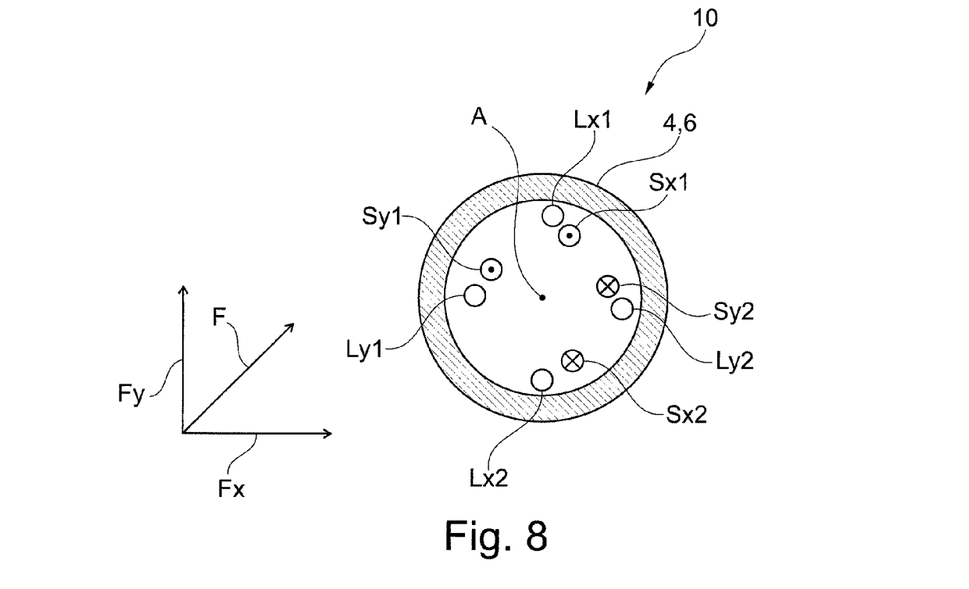
FIG. 8 is a cross section of this load pin.

The configuration of the direction sensitive magnetic field sensors LX1, LX2, LY1, LY2 is explained in more detail by making reference to the simplified cross section of the load pin 10, which is shown in FIG. 8. The cross sectional plane is arranged to be substantially perpendicular to the shaft axis A. The first direction sensitive sensor LX1 and the third direction sensitive sensor LX2 form a first group of magnetic field sensors. The second group of sensors consists of the second direction sensitive sensor LY1 and the fourth direction sensitive sensor LY2. The sensing direction SX1 of the first sensor LX1 is 180° opposite to the third sensing direction SX2 of the third sensor LX2. This is indicated in the figure using the conventional signs. The first sensing direction SX1 points out of the paper plane, the third sensing direction SX2 points into the paper plane. Similar to the first group of sensors LX1, LX2, the second sensing direction SY1 and the fourth sensing direction SY2 are 180° opposite to each other. The second and fourth sensor LY1, LY2 are arranged accordingly. As it is indicated using the commonly known direction signs, the second sensing direction SY1 points out of the paper plane while the fourth sensing direction SY2 is directed into the paper plane.

The second sensor LY1 having the second sensing direction SY1 and the fourth sensor SY2 having the fourth sensing direction SY2 are shown in the simplified cross section of FIG. 7. The first sensor LX1 and the first sensing direction SX1 are added to the simplified cross section of FIG. 7 solely for clarification of the configuration of the sensors. Naturally, the first sensor LX1 is not arranged in a common plane with the second and fourth sensor SY1, SY2, as it is shown in the cross section of FIG. 8.

Figure 9:
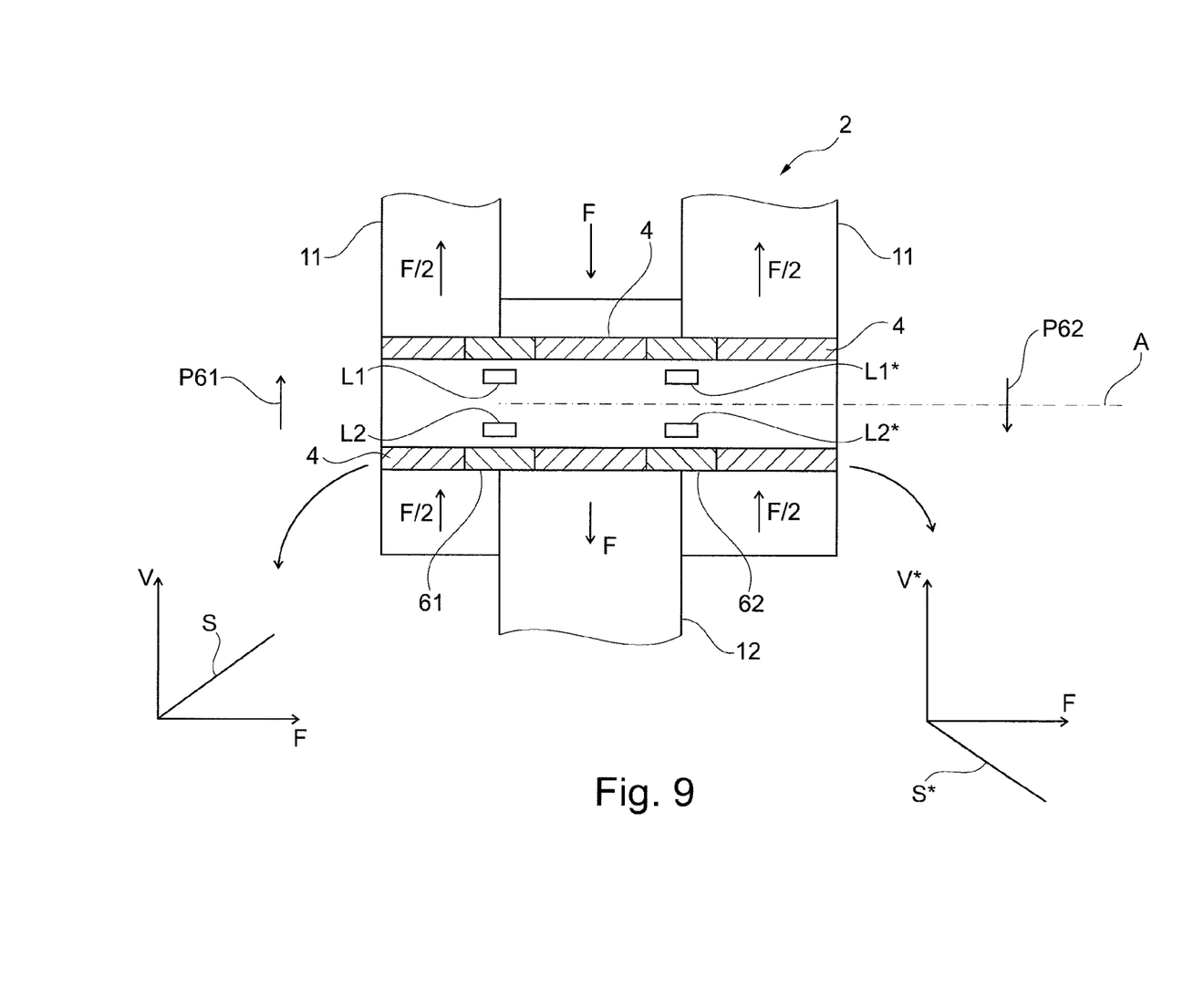
FIG. 9 is a simplified cross section of a magneto-elastic sensor according to an embodiment of the invention.

When the shaft like member 4 is exposed to the first and second shear stress forces FS1, FS2, the signals of the first group of sensors (comprising the first and the third sensor LX1, LX2) is analyzed so as to determine a first component of a force F inducing the respective shear stress forces FS1, FS2. In a Cartesian coordinate system, this first component may be indentified with the X-component FX of the applied force F. This is illustrated in FIG. 9). The evaluation of the measurement values of the sensors of the second group (i.e. the second sensor LY1 and the fourth sensor LY2) results in a value for a second component of the force F. Within the same Cartesian coordinate system, this second force is identified with the Y-component of the force F, i.e. the force component FY.

Using the load pin 10 according to this embodiment of the invention, the amount and the direction of an applied force F can be determined. According to another embodiment of the invention (not shown), the direction sensitive sensors have sensing directions, which are substantially perpendicular to the shaft axis A. This sensor configuration may be achieved by for example selecting and rotating the first and third sensor SX1, SX2 by 90° with respect to the shaft axis A. According to this particular embodiment of the invention, the load pin 10 is suitable for determination of a force introducing compressive or tensile stress in axial direction.

FIG. 9 is a cross section of a magneto-elastic sensor 2 according to another embodiment of the invention. The first member 11 surrounds the second member 12, which is exposed to a force F. The sleeve like first member 11 takes up the counteracting force, which means that each side of the member 11 takes up a force of F/2. The longitudinally extending shaft like member 4 intersects the first and the second member 11, 12 along the shaft axis A. The shaft like member 4 comprises a first magneto-elastically active region 61 and a second magneto-elastically active region 62. Similar to the other embodiments of the invention, these are directly or indirectly attached to or form a part of the member 4 in such a manner that the mechanic stress is transmitted to the active regions 61, 62. The active regions 61, 62 are magnetically polarized in opposite direction. This is illustrated by the first polarization P61 of the first active region 61 and the second polarization P62 of the second active region 62. The magnetic polarizations P61, P62 are substantially 180° opposite to each other. Furthermore, they are substantially perpendicular to the shaft axis A.

A first pair of magnetic field sensors comprising a first sensor L1 and a second sensor L2 is arranged inside the shaft like member 4 in that this pair of sensors cooperates with the first active region 61. Similar, a second pair of magnetic field sensors comprising a first and a second sensor L1* and L2* is arranged inside the shaft 4 so as to interact with the second active region 62. The sensors L1, L2 of the first pair and the sensors L1*, L2* of the second pair are arranged approximate the first and the second magneto-elastically active region 61, 62, respectively. The first sensor pair L1, L2 outputs a first signal S, which is illustrated as a voltage V varying with the applied force F in the lower left of FIG. 9. The signal S corresponds to a stress-induced magnetic flux emanating from the first magnetically polarized region 61.

Similarly, the second pair of magnetic sensors L1*, L2* outputs a second signal S* corresponding to a stress-induced magnetic flux emanating from the second magnetically polarized region 62. This signal S* is also a voltage V* varying with the applied F (see lower right of FIG. 9). However, the slope of the second signal S* is opposite to that of the first signal S. A control unit (not shown) of the magneto-elastic sensor 2 is configured for determination of the force F inducing a stress in the member 4. The control unit performs a differential evaluation of the signals S and S* of the first pair of sensors L1, L2 and the second pair of sensors L1*, L2*. This differential evaluation advantageously doubles the sensitivity of the signal, which is correlated with the applied stress. Because the polarization P61 and P62 of the first and second magnetically active region 61, 62 is opposite to each other, theoretically possible external fields are compensated. The magneto-elastic sensor 2 according to this embodiment is more sensitive and less susceptible to errors.

Advantageously, all embodiment of the invention may be equipped with the sensor configuration of FIG. 9 having separate, oppositely polarized active regions 61, 62 and two corresponding sets i.e. pairs of sensors L1, L2 and L1*, L2*.

Furthermore, the embodiment of FIG. 9 may be equipped with the sensor configuration, which is known from the load pin in FIG. 8. In other words, the sensor pairs L1, L2 and L1*, L2* may be replaced by a sensor configuration having four sensors LX1, LX2, LY1, LY2, which is exemplarily shown in FIGS. 7 and 8. According to this particular embodiment of the invention, additional force vectors may be determined.

Figure 10:
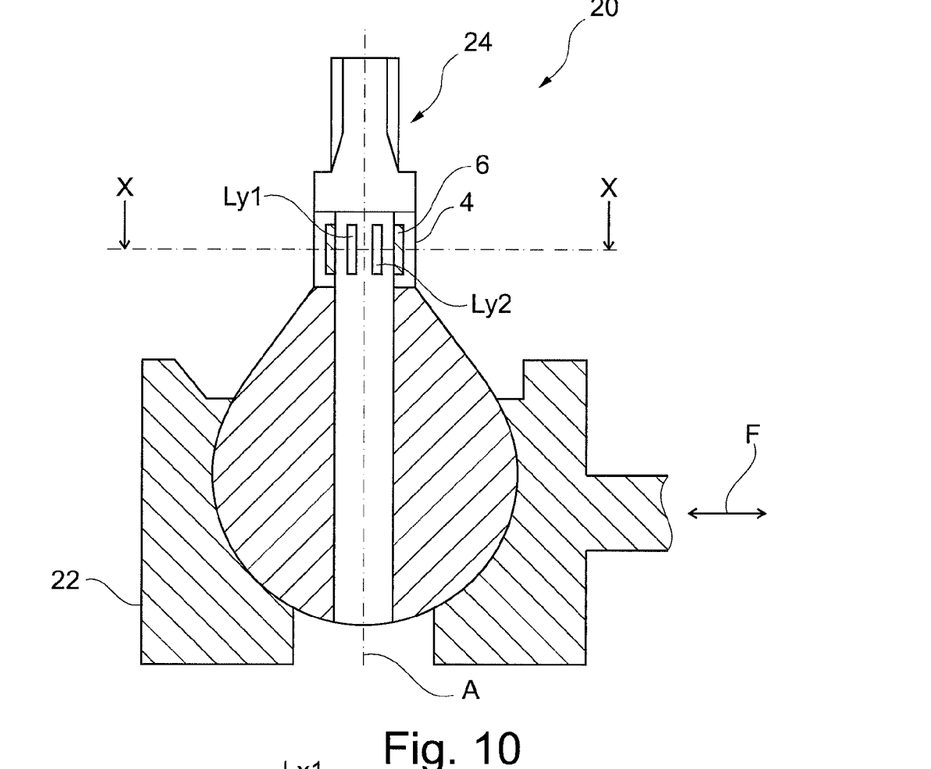
FIGS. 10 and 12 show simplified axial cross sections of a ball joint, according to embodiments of the invention.
Figure 11:
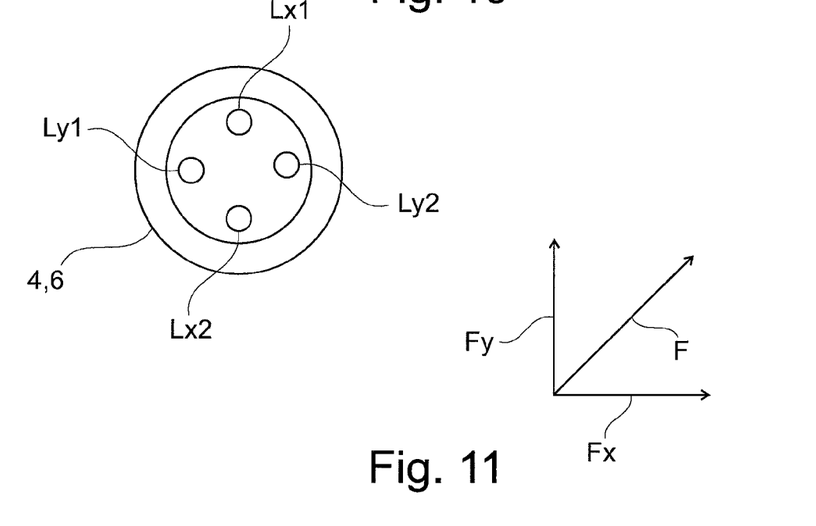
FIGS. 11 and 13 show cross sections along the cutting line denoted X-X in FIG. 10 and cutting line XII-XII in FIG. 12, respectively.

FIG. 10 is a simplified cross section of a ball-joint 20, according to another embodiment of the invention. The ball-joint 20 comprises a socket 22 holding a bearing stud 24 having a shaft like member 4 incorporating a sensor system. FIG. 11 is the corresponding cross section along the plane X-X. When a force F is applied to the ball-joint 20, the shaft like member 4 is subject to various loads. The sensor system of the ball-joint 20 according to the embodiment in FIGS. 10 and 11 is configured for shear stress detection. In general, the shear stress detection operates similar to the detection of the shear stress in the load pin of FIGS. 7 and 8.

The shaft like member 4 of the ball-joint 20 incorporates four direction sensitive sensors LX1, LX2, LY1, LY2. Again, the first and third magnetic field sensor LX1, LX2 form the first group of sensors, which is for determination of the first component FX of the applied force F (see FIG. 11). The second group of sensors, which comprises the second and fourth direction sensitive magnetic field sensor LY1, LY2, is configured for determination of the second component FY of the applied force F. The sensing direction (not shown) of the first to fourth sensor LX1, LX2, LY1, LY2 is configured similar to FIG. 8. In other words, the sensing direction of LX1 and LY1 point out of the paper plane. The sensing direction of LY2 and LX2 point into the paper plane.

Figure 12:
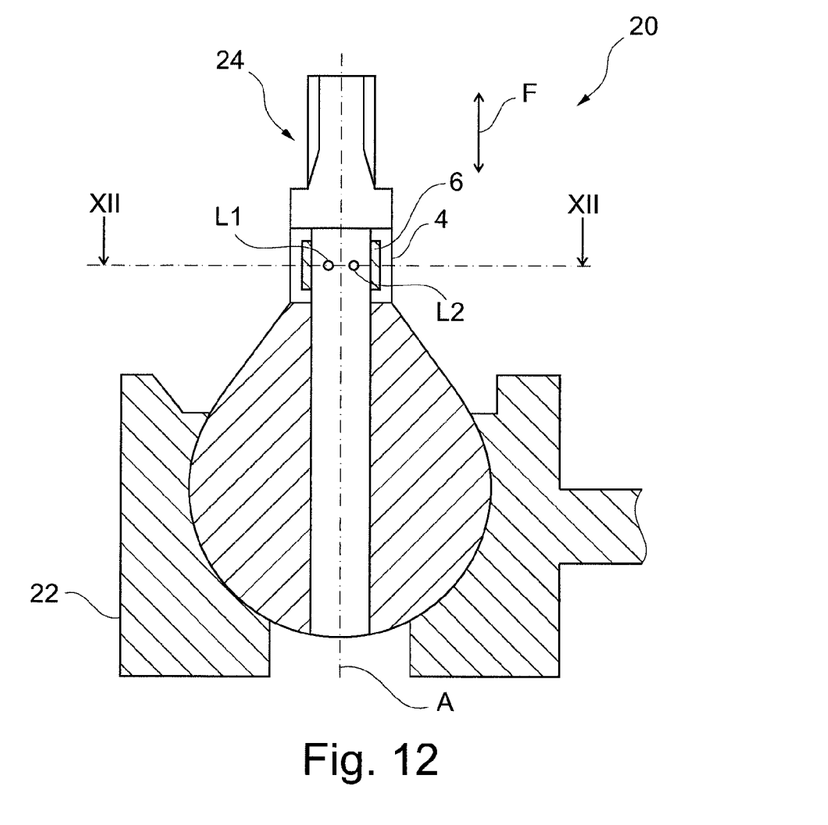
Figure 13:
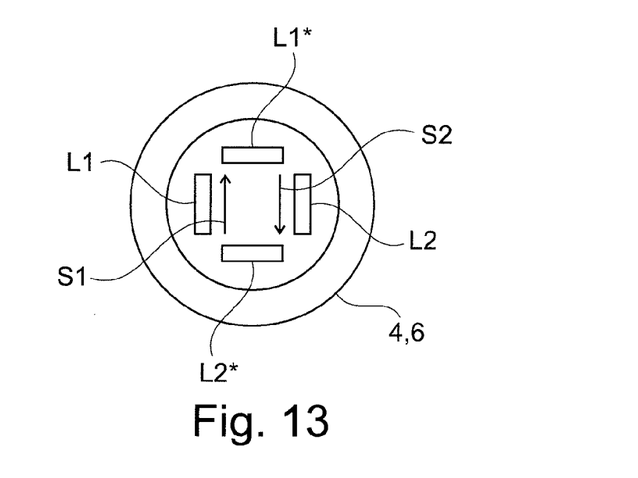

FIG. 12 and FIG. 13 illustrate a ball-joint 20 according to another embodiment of the invention. FIG. 12 is a simplified axial cross section along the plane XII-XII in FIG. 13. The sensor system, which is incorporated in the shaft like member 4, comprises a first to fourth direction sensitive magnetic field sensor L1, L2, L1* and L2*. The direction sensitive sensors L1, L2, L1*, L2* are tilted by 90° with respect to the shaft axis A, when compared to the sensors LX1, LX2, LY1 and LY2 of the embodiment in FIGS. 10 and 11. The sensing directions of the magnetic field sensors, only two of which are shown solely for clarity reasons (see S1, S2 of the first and second sensor L1, L2), are substantially perpendicular to the shaft axis A of the shaft like member 4. Furthermore, the sensing directions of the sensor pairs L1 and L2, i.e. S1 and S2 are 180° opposite to each other. Similarly, the sensing directions (not shown) of the second sensor pair S1* and S2* are substantially 180° opposite to each other. This is further illustrated in the simplified cross section of FIG. 13. Similar to the embodiment of FIG. 8, the sensor arrangement in FIGS. 12 and 13 is configured for determination of tensile and compressive stress in various directions. In other words, the measurement values of the sensor pairs L1, L2 and L1*, L2* may be evaluated so as to determined the component of the stress vector.

The sensor system of the ball-joint 20 according to this embodiment is configured for determination of an axial force F. Due to the inverse sensing directions S1, S2 of the first and second sensor L1, L2, the value and the prefix, i.e. the direction, of the axially directed force F can be determined.

Figure 14:
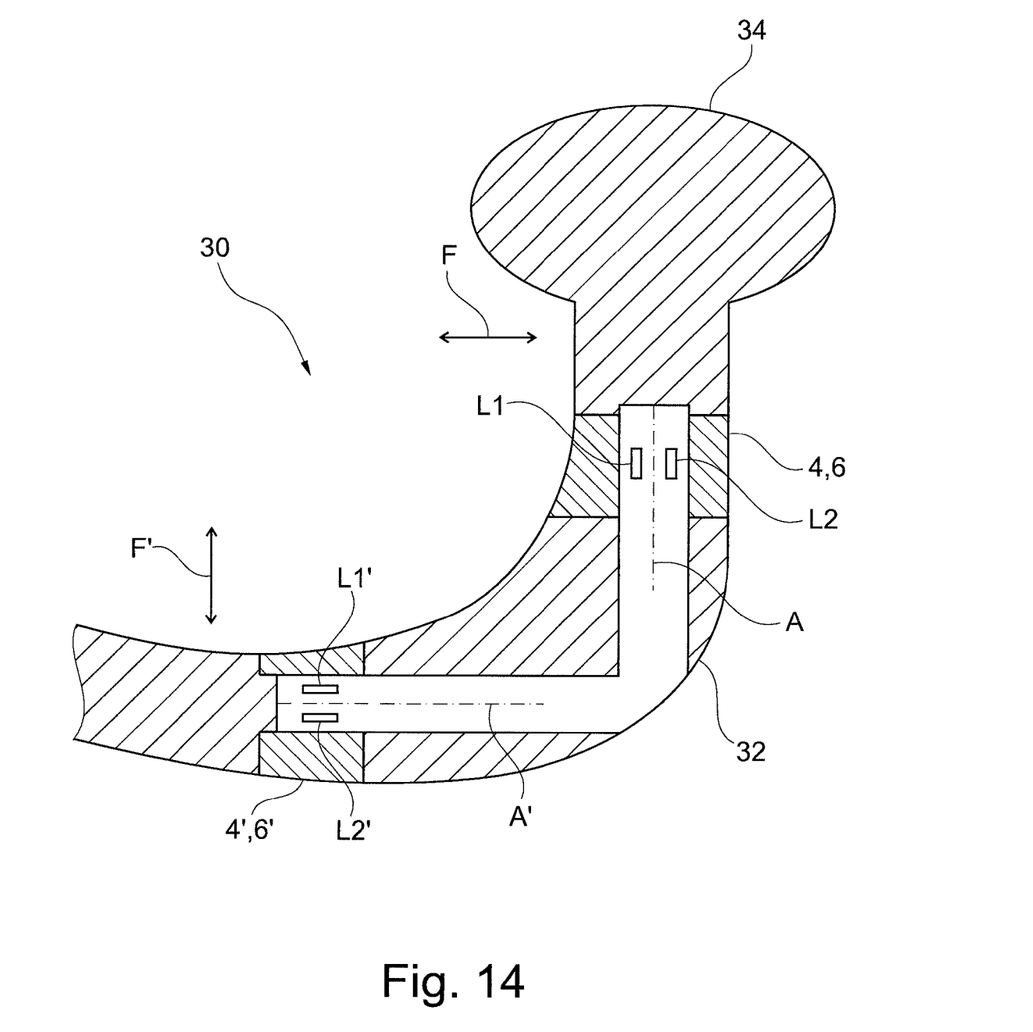
FIGS. 14 and 15 show simplified axial cross sections of tow couplings, according to embodiments of the invention.

FIG. 14 is a simplified cross section showing a tow coupling 30, according to an embodiment of the invention. The tow coupling 30 comprises a curved shaft 32 carrying a tow ball 34. The shaft 32 of the tow coupling 30 incorporates a first shaft like member 4 and a second shaft like member 4'. A respective one of the shaft like members 4, 4' comprises a magneto-elastically active region 6, 6' emanating a stress induced magnetic field vector, which is detectable by a sensor arrangement. The first shaft like member 4 comprises a first and a second direction sensitive magnetic field sensor L1, L2, which are configured for detection of a towing force F. The first and second sensor L1, L2 in this first shaft like member 4 are arranged in that their sensing directions (not shown) are substantially parallel to the first shaft axis A.

The second sensor system, which is incorporated in the second shaft like member 4', also comprises a first and a second direction sensitive sensor L1', L2', both of which are arranged to have a sensing direction (not shown), which is substantially parallel to the second shaft axis A'. This second sensor system is configured to detect a supporting force F' of the tow coupling 30.

The two sensor systems, which reside in the first and second shaft like member 4, 4', respectively, can be equipped additional sensors in that each system comprises four direction sensitive magnetic field sensors. Such a sensor configuration is explained in more detail with reference to FIGS. 7 and 8. When this configuration is transferred to this embodiment, the corresponding transverse forces of the force F and F' are also detectable.

Figure 15:
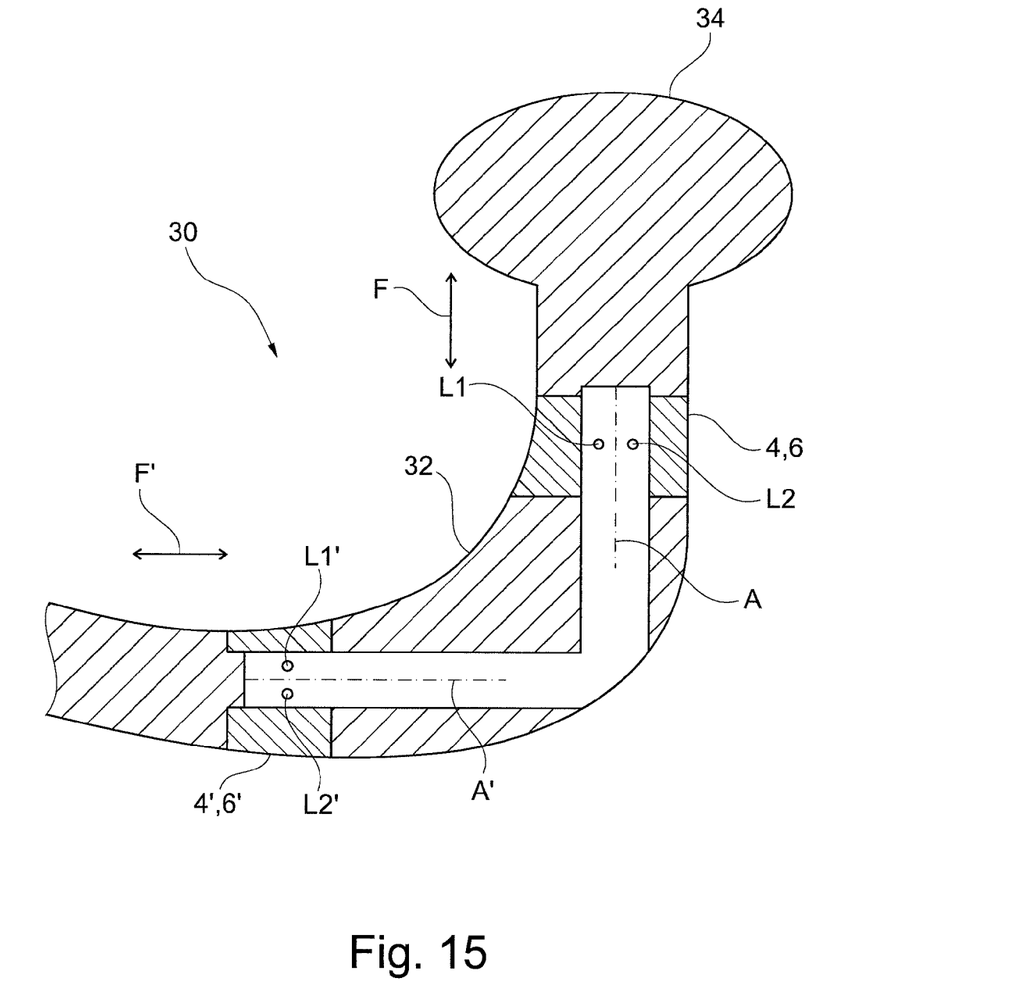

In the simplified cross section of FIG. 15, there is another embodiment of a tow coupling 30. The direction sensitive magnetic field sensors L1, L2, L1', L2' are rotated by 90° with respect to the respective shaft axis A, A', when compared to the embodiment of FIG. 14. The first and second direction sensitive magnetic field sensor L1, L2 of the first sensor system, which is arranged in the first shaft like member 4, have sensing directions (not shown) which are preferably 180° opposite to each other and which are substantially perpendicular to the shaft axis A. The second sensor system, which is incorporated in the second shaft like member 4', comprises a first and second direction sensitive magnetic field sensor L1', L2' having sensing directions, which are preferably 180° opposite to each other and which are substantially perpendicular to the second shaft axis A'. The first sensor system (i.e. the first and second sensor L1, L2) is configured for determination of a supporting force F. The second sensor system is configured for determination of a towing force F'.

Furthermore, the tow couplings according to the embodiment of FIG. 14 may be equipped with a sensor configuration, which is known from the load pin in FIG. 8. In other words, the sensors, which reside in the first and in the second shaft like member 4, 4' may be sensor configurations, each having four sensors LX1, LX2, LY1, LY2 having sensing directions, which are substantially parallel to the shaft axis A and A', respectively. The sensor configuration, which is shown for a load pin in FIGS. 7 and 8 may be applied in the tow coupling 30 as well. According to this particular embodiment of the invention, additional force vectors may be determined.

The tow coupling 30 according to the embodiment of FIG. 15 may be equipped with a sensor configuration, which is known from FIG. 13. In other words, the sensors, which reside in the first and in the second shaft like member 4, 4' may be sensor configurations, each having four sensors L1, L2, L1* and L2* having sensing directions, which are substantially perpendicular to the shaft axis A and A', respectively. The sensor configuration, which is shown for the ball joint in FIGS. 12 and 13 may be applied in the tow coupling 30 of FIG. 15 as well. According to this particular embodiment of the invention, additional force vectors may be determined.

The sensors L1, L2, L1', L2' of the tow coupling 30 are preferably arranged inside the hollow curved shaft like member 32 of the tow coupling 30.

The direction sensitive sensors L1, L2, L1', L2', L1*, L2*, LX1, LX2, LY1, LY2 may be vector sensors. In particular, Hall-effect, magneto-resistance, magneto-transistor, magneto-diode, MAGFET field sensor or fluxgate magneto-meter sensors can be applied. This advantageously applies to all embodiments of the invention.

The magneto-elastic sensor according to aspects of the invention is advantageously applicable for load measurement in cranes, for overload detection in elevators, for load detection in farming equipment, for load detection in construction equipment, for load detection in chassis applications or for load detection in a fork lifter.

In addition to this, the magneto-elastic sensor is advantageously applicable in suspension applications for load detection, load detection for cable cars, load detection for railroad applications and load detection for cable forces. Furthermore, it is applicable for flap load detection, for load detection in hydraulic cylinders, for structural load detection, line tension detection, sheave or pulley load detection or shackle load detection. In addition to this, the magneto-elastic sensor is advantageously applicable for towing or pulling load detection and/or for brake force detection.

The magneto-elastic sensor may be integrated into a hoisting gear or in a winch, in cable laying equipment, marine tankers or in offshore platforms. A rope, a chain and/or a brake anchor, bearing blocks, a pivot and/or a shackle may be provided with the magneto-elastic sensor according to aspects of the invention.

A floor conveyor, a sprocket axle, front end loaders, railroad couplings, conveyor belt rollers, clevis joints, crane cargo hooks, a tow bar connection, a rail points load pin and/or connecting rod may include the magneto-elastic sensor according to embodiments of the invention. The mooring line tension or a tow line tension may be determined.

It is understood that a respective one of the mentioned entities may be advantageously equipped with the sensor according to aspects of the invention. In particular these entities may comprise a load pin according to aspects of the invention, this applies for example to marine or industrial equipment.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

The invention claimed is:

1. A magneto-elastic sensor comprising:
   a longitudinally extending shaft like member, which is subject to a load introducing mechanic stress in the member,
   at least one magneto-elastically active region directly or indirectly attached to or forming a part of the member in such a manner that the mechanic stress is transmitted to the active region, said active region comprising at least one magnetically polarized region such that the polarization becomes increasingly helically shaped as the applied stress increases;
   a magnetic field sensor means arranged approximate the at least one magneto-elastically active region for outputting a signal corresponding to a stress-induced magnetic flux emanating from the magnetically polarized region;
   the magnetic sensor means comprising at least one direction sensitive magnetic field sensor, which is configured for determination of at least one out of a shear stress and a compressive stress, wherein the magnetic field sensors are arranged to have a predetermined and fixed spatial coordination with the member, wherein the member is an at least partially hollow shaft and all magnetic field sensors of the magnetic sensor means are entirely arranged inside an interior of the hollow shaft.

2. The magneto-elastic sensor of claim 1, wherein the direction sensitive magnetic field sensor is arranged in that a sensing direction of the magnetic field sensor is at least substantially parallel to a tangential direction of the shaft like member or in that the sensing direction of the magnetic field sensor is at least substantially parallel to a radial direction of the shaft like member.

3. The magneto-elastic sensor of claim 1, wherein the magnetic sensor means comprises a first and a second direction sensitive magnetic field sensor having 180° opposite sensing directions.

4. The magneto-elastic sensor of claim 3, wherein the first and the second magnetic field sensor are arranged approximate to opposite sides of the magneto-elastically active region, respectively, wherein said sides of the magneto-elastically active region are opposite to each other with respect to the shaft axis.

5. The magneto-elastic sensor of claim 1, wherein the sensor means comprises at least four magnetic field sensors having a first to fourth sensing direction, wherein the sensing directions and a shaft axis are at least substantially parallel to each other, and wherein the first to fourth magnetic field sensor are arranged along the circumference of the shaft having substantially equal distances in circumferential direction between each other.

6. The magneto-elastic sensor of claim 5, wherein the first and third magnetic field sensor are arranged opposite to each other with respect to the shaft axis and the first and third sensing direction are arranged 180° opposite to each other, and wherein the second and fourth magnetic field sensor are arranged opposite to each other with respect to the shaft axis and the second and fourth sensing direction are arranged 180° opposite to each other.

7. The magneto-elastic sensor of claim 1, wherein the at least one magneto-elastically active region projects along a circumference of the member, and wherein said region is magnetized in that the domain magnetizations in the magnetically polarized region lie within at most a plus or minus 45° limit of a circumferential direction of the member.

8. A magneto-elastic sensor comprising:
a longitudinally extending shaft like member, which is subject to a load introducing mechanic stress in the member,
at least one magneto-elastically active region directly or indirectly attached to or forming a part of the member in such a manner that the mechanic stress is transmitted to the active region, said active region comprising at least one magnetically polarized region such that the polarization becomes increasingly helically shaped as the applied stress increases;
a magnetic field sensor means arranged approximate the at least one magneto-elastically active region for outputting a signal corresponding to a stress-induced magnetic flux emanating from the magnetically polarized region;
the magnetic sensor means comprising at least one direction sensitive magnetic field sensor, which is configured for determination of at least one out of a shear stress and a compressive stress, wherein the magnetic field sensors are arranged to have a predetermined and fixed spatial coordination with the member,
wherein the member comprises a first magneto-elastically active region and a second magneto-elastically active region, which are directly or indirectly attached to or form a part of the member in such a manner that the mechanic stress is transmitted to the active regions, each active region comprising a magnetically polarized region, wherein the magnetic polarization of the first active region and the magnetic polarization of the second active region are substantially opposite to each other, and wherein the magnetic sensor means comprises a first pair of magnetic sensors comprising a first and a second magnetic field sensor being arranged approximate the first magneto-elastically active region for outputting a first signal corresponding to a stress-induced magnetic flux emanating from the first magnetically polarized region and the magnetic sensor means comprises a second pair of magnetic sensors comprising a first and a second magnetic field sensor being arranged approximate the second magneto-elastically active region for outputting a second signal corresponding to a stress-induced magnetic flux emanating from the second magnetically polarized region, wherein the magneto-elastic sensor further comprises a control unit, which is configured for determination of the stress applied to the member by performing a differential evaluation of the signals of the first pair of sensors and the second pair of sensors.

9. A load pin having a longitudinally extending shaft like member incorporating the magneto-elastic sensor of claim 1 or 8.

10. A ball-joint having bearing stud and socket, the bearing stud comprises a longitudinally extending shaft like member incorporating a magneto-elastic sensor according to any one of claims 1 or 8.

11. A tow coupling having a curved shaft and a tow-ball, the curved shaft comprising at least one longitudinally extending shaft like member incorporating a magneto-elastic sensor according to any one of claims 1 or 8, wherein the curved shaft comprises a first and a second longitudinally extending shaft like member, the shaft axes of which are substantially perpendicular to each other, wherein the first and the second longitudinally extending shaft like member each incorporate a magneto-elastic sensor according to-any one of claims 1 or 8.

12. A method of determining a direction of a load vector, the method comprising the steps of:
providing a magneto-elastic sensor comprising: a longitudinally extending shaft like member, which is subject to the load introducing mechanic stress in the member; at least one magneto-elastically active region directly or indirectly attached to or forming a part of the member in such a manner that the mechanic stress is transmitted to the active region, said active region comprising at least one magnetically polarized region such that the polarization becomes increasingly helically shaped as the applied stress increases; a magnetic field sensor means arranged approximate the at least one magneto-elastically active region for outputting a signal corresponding to a stress-induced magnetic flux emanating from the magnetically polarized region; wherein the magnetic sensor means comprises at least one direction sensitive magnetic field sensor, which is arranged to have a predetermined and fixed spatial coordination with the member,
exposing the longitudinally extending shaft like member to the load,
processing measurement data of the at least one direction sensitive magnetic field sensor so as to determine at least one out of a shear stress and a compressive stress, so as to determine a direction of the load vector from the measurement data and the predetermined and known spatial coordination between the direction sensitive magnetic field sensor and the member,
wherein the sensor means comprises at least a first to fourth magnetic field sensor having a first to fourth sensing direction, wherein the sensing directions and a shaft axis are at least substantially parallel to each other, and wherein the first to fourth magnetic field sensor are arranged along the circumference of the shaft having substantially equal distances in circumferential direction between each other, the method further comprising the steps of:

processing measurement data of the first and third magnetic field sensor so as to determine a first component of a load vector and processing measurement data of the second and fourth magnetic field sensor so as to determine a second component of the load vector, determining a direction of the load vector, which impacts the longitudinally extending shaft like member, from the determined first and second component and the predetermined and known spatial coordination of the first to fourth magnetic field sensor with respect to the member.

13. A method of determining a direction of a load vector, the method comprising the steps of:

providing a magneto-elastic sensor comprising: a longitudinally extending shaft like member, which is subject to the load introducing mechanic stress in the member; at least one magneto-elastically active region directly or indirectly attached to or forming a part of the member in such a manner that the mechanic stress is transmitted to the active region, said active region comprising at least one magnetically polarized region such that the polarization becomes increasingly helically shaped as the applied stress increases; a magnetic field sensor means arranged approximate the at least one magneto-elastically active region for outputting a signal corresponding to a stress-induced magnetic flux emanating from the magnetically polarized region; wherein the magnetic sensor means comprises at least one direction sensitive magnetic field sensor, which is arranged to have a predetermined and fixed spatial coordination with the member, exposing the longitudinally extending shaft like member to the load, processing measurement data of the at least one direction sensitive magnetic field sensor so as to determine at least one out of a shear stress and a compressive stress, so as to determine a direction of the load vector from the measurement data and the predetermined and known spatial coordination between the direction sensitive magnetic field sensor and the member, wherein the member comprises a first magneto-elastically active region and a second magneto-elastically active region, which are directly or indirectly attached to or form a part of the member in such a manner that the mechanic stress is transmitted to the active regions, each active region comprising a magnetically polarized region, wherein the magnetic polarization of the first active region and the magnetic polarization of the second active region are substantially opposite to each other, and wherein the magnetic sensor means comprises a first pair of magnetic sensors comprising a first and a second magnetic field sensor being arranged approximate the first magneto-elastically active region for outputting a first signal corresponding to a stress-induced magnetic flux emanating from the first magnetically polarized region and the magnetic sensor means comprises a second pair of magnetic sensors comprising a first and a second magnetic field sensor being arranged approximate the second magneto-elastically active region for outputting a second signal corresponding to a stress-induced magnetic flux emanating from the second magnetically polarized region, the method further comprising the step of:

performing a differential evaluation of the signals of the first pair of sensors and the second pair of sensors so as to determine the stress applied to the member.

* * * * *